(12) United States Patent
Adams

(10) Patent No.: US 8,162,819 B2
(45) Date of Patent: Apr. 24, 2012

(54) METHOD AND DEVICE TO PROVIDE PENIS ENLARGEMENT

(76) Inventor: Kenneth W. Adams, Ontario (CA)

(*) Notice: Subject to any disclaimer, the term of this patent is extended or adjusted under 35 U.S.C. 154(b) by 640 days.

(21) Appl. No.: 11/989,728

(22) PCT Filed: Aug. 11, 2006

(86) PCT No.: PCT/CA2006/001333
§ 371 (c)(1),
(2), (4) Date: Feb. 24, 2009

(87) PCT Pub. No.: WO2007/019687
PCT Pub. Date: Feb. 22, 2007

(65) Prior Publication Data
US 2009/0287041 A1    Nov. 19, 2009

(30) Foreign Application Priority Data
Aug. 12, 2005   (CA) ................................ 2515883

(51) Int. Cl.
*A61F 5/00* (2006.01)
(52) U.S. Cl. ............................................. 600/38
(58) Field of Classification Search .............. 600/38–41; 128/897, 898
See application file for complete search history.

(56) References Cited

U.S. PATENT DOCUMENTS
5,020,796 A * 6/1991 Ullmann ....................... 482/126
6,033,374 A * 3/2000 Miller, Jr. ....................... 602/36

FOREIGN PATENT DOCUMENTS
| CA | 2306104 A1 | 4/1999 | |
| CA | 2884439 A1 | 3/2001 | |
| CA | 2444663 A1 | 3/2005 | |
| JP | 2001269361 | * 10/2001 | .................. 600/38 |

OTHER PUBLICATIONS

Machine generated english language translation of JP 2001-269361, 11 pages.*

* cited by examiner

*Primary Examiner* — Samuel Gilbert
(74) *Attorney, Agent, or Firm* — Manelli Selter PLLC; Edward J. Stemberger

(57) ABSTRACT

A penis tensioning device effecting penis tissue modeling and penis enlargement, the device comprising an elongate tensioning, biasing member having a first portion (14) and a second portion; first retaining means connected to the first portion (14) and Cooperable in tight-fitting engagement with a portion of the penis adjacent the head; second retaining means connected to the second portion and cooperable with a distal member selected from the group consisting of an article of clothing, a body part and an inanimate object.

12 Claims, 6 Drawing Sheets

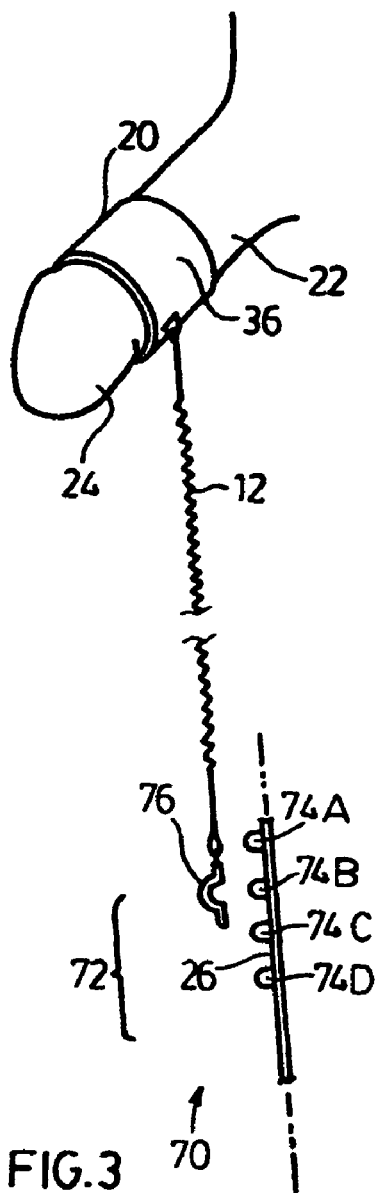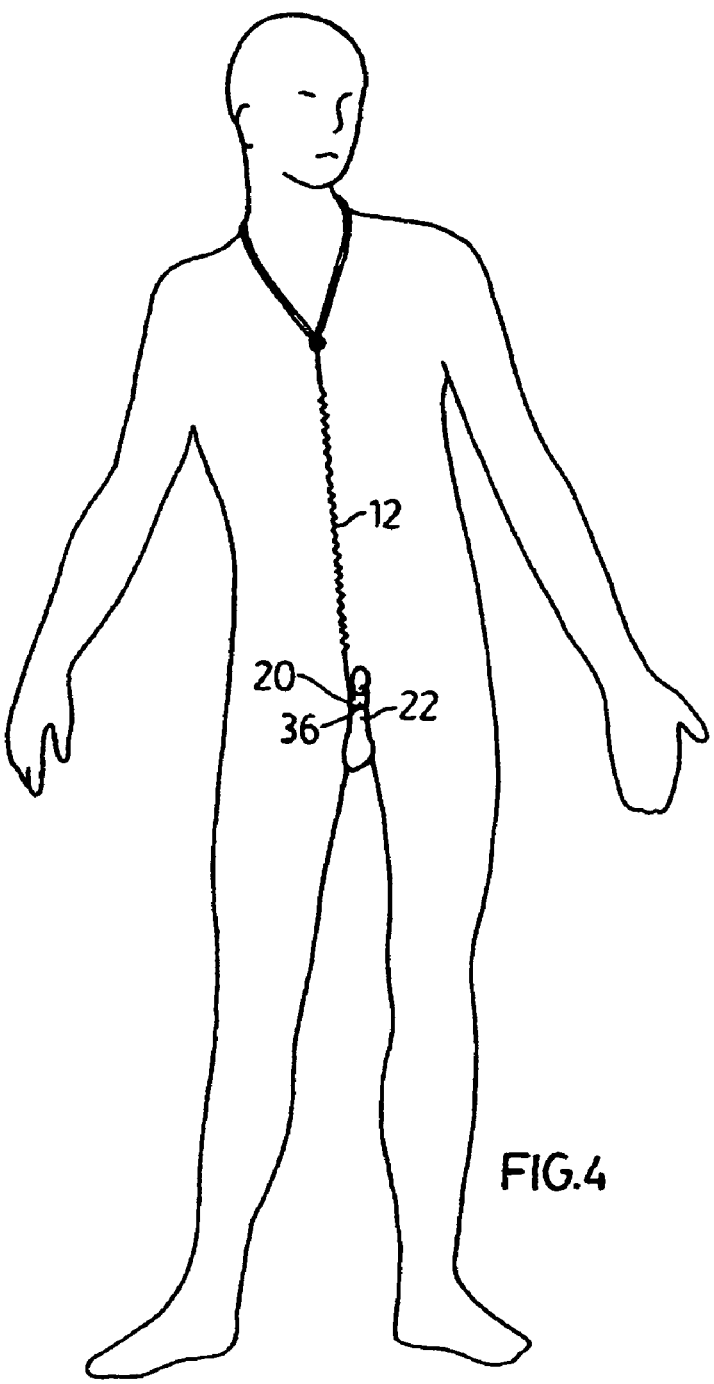
FIG.3
FIG.4

METHOD AND DEVICE TO PROVIDE PENIS ENLARGEMENT

FIELD OF THE INVENTION

This invention relates to a method and device to effect penis enlargement, particularly when the device is worn by a man while being active.

BACKGROUND OF THE INVENTION

There are various circumstances under which a male subject may desire the permanent enlargement of the length and/or girth of his penis, in both its flaccid and erect states. Penis enlargement may be desired for medical reasons, for example, if a patient is unable to penetrate during coitus due to an unusually small penis size; for cosmetic reasons; or to improve a man's self-esteem.

There are numerous examples of devices that generate real tissue growth by generating and applying biologically significant forces to tissues of the human body. Examples are the tissue expanders used to expand the skin to cover areas of tissue loss in plastic and other cosmetic surgical procedures. Also, traction devices are used for limb lengthening to stimulate the natural tissue remodeling that occurs during the actual growth of other body parts. In orthodontic dental treatments, biological forces are used routinely to stimulate true tissue remodeling and growth.

There have been several attempts to create a safe and effective means for achieving permanent penis enlargement, including the use of external weights, traction devices and suction devices, as well as pharmacological therapies to use the nature veno-occlusive mechanism to generate biologically significant forces within the penis to cause penis growth. The use of external weights is cumbersome and generally impractical and produces localized compressive forces that may cause localized ischemia. Furthermore, use of weights often leads to a thinning of the penis and may even impair penis function. In addition to weights, traction devices have also been tried. For example, the "PeniStretcher™" device is one such device, which uses a rigid frame and springs to generate mechanical forces to the penis. Several disadvantages are inherent to the design of these mechanical devices. Some of these problems are described as follows:

The mechanical devices invariably have rigid parts that are bulky and hence protrude out from the body and cause bulges even if they are covered by clothing. Thus, they generally cannot be discretely concealed by clothing and the wearer of such a device cannot freely go about his daily activities. Since the effectiveness of these devices is generally directly proportional to the duration of time these devices are worn, limiting the amount of time that these devices can be worn limits the duration and effectiveness of these devices.

These devices also tend to be unidirectional since their basic designs functionally create forces that are unidirectional, i.e. the direction of the vector of the forces they generate is relatively static and directionally restricted in terms of the angulation of the vector which represents the way the forces they generate in the penis are applied relative to pelvic bones on the body. For example, weights are generally only functional when the man is standing and generate a force acting downward. When the "PeniStretcher" device is attached to the body, the penis is usually pulled out unsatisfactorily horizontally away from the body, and parallel to the ground when standing. In contrast, a device that allows the direction of the forces being applied to the penis to be re-directed relative to the pelvic bones allows more precise control over how the mechanical forces acting on the penis would stimulate the growth and remodeling in the penis. By changing the direction of the forces acting upon the penis there would be increased control over how those forces were distributed within the penile tissues and how and where the growth occurred could be more accurately controlled. If the penis is manually pulled in different directions a man can feel majority of the force being isolated to different fibrous bands within the penis to the pelvic bones. When the penis is pulled, for example by manually grasping the head of the penis to the right or left, or up or down and if the man palpates the structures under tension inside the penis using his free hand, he can clearly feel that as the direction of the applied tension changes, entirely different fibrous regions/structures within the penis are put under tension while adjacent regions structures feel lax and unstressed as the direction of the force he applies to the penis changes.

Further, the forces provided by these prior art devices cannot be easily or simply varied. With the "PeniStretcher™" device or with typical weight systems, when the device is applied to the body there is no way to precisely control and to maintain that same level of force consistently over a relatively long period of time. Further, the ability to alter the forces being generated to the penis in a defined measurable way is not possible for the currently available devices. In contrast, a device that could have the forces readily changed would provide an advantage.

Yet further, the use of metals and other rigid materials used in the fabrication of these prior art devices have a substantial mass to them which is maximal in the weight systems that use mass and gravity to generate the forces acting on the penis. This is present in all the devices currently on the market Physical activities that involve movement or change of direction generates potentially harmful accelerative forces to the penis since these devices are attached to the body of the user. Hence, there are significant restrictions on the types of physical activities performed by the wearer when using these devices. A lightweight device that generates forces that are a small fraction of the therapeutic forces created by the device under maximal accelerations of the body, such as jumping and sudden stopping, will allow the user unlimited physical activity when using a device with minimal weight to such a device.

Suction devices are also cumbersome and impractical to wear on a prolonged basis, have limited effectiveness, and pose a number of risks. Suction devices produce localized compressive forces that may cause localized ischemia. Vacuum seals with pressure over 20 mm Hg can obstruct capillary flow and inhibit tissue perfusion. Suction devices often come with warnings that the devices should not be used for periods exceeding 20-30 minutes, which may be insufficient to achieve the desired result. Use of suction devices can also result in the thickening of the skin and accumulation of fluid in the superficial layers of the skin and subdermis. The skin of the penis is hypermobile, and only very loosely connected to deeper connective tissues and structures that comprise the erectile tissues of the penis. The skin of the penis can readily separate from the fibrous connective tissue capsule, which encloses the erectile tissue of the penis when externally applied suction forces are applied to the penis.

Also, any suction forces applied to the penis has a proportionately larger effect on the skin, and the forces on the deeper structures diminish dramatically. The increase in the surface area of the skin causes the suction forces to be applied mainly to the skin, not to the erectile tissue and the surrounding capsule of the cavernosal tissue. As a result, the skin can be thickened as fluid is extravasated and there is typically no, or only a limited enlargement, of the underlying erectile tissues of the penis. Use of suction devices may also cause the separation of the skin from the subdermis and the formation of seromas or blisters on the penis. The application of suction devices to the penis may also cause the extravasation of red blood cells out of the vascular spaces and into the extracellular compartments. If vacuum devices are applied for extended periods of time, this may lead to a significant pigmentation of the penis. Also applying a suction device repeatedly may cause the deposition of large amounts of iron and other hemoglobin degradation products in the tissue of the penis causing hemosiderosis, which ultimately results in fibrosis. Furthermore, erectile dysfunction may result from prolonged use of these devices.

There is, therefor, a need for a penis enlargement method and device, which do not suffer from any of the aforesaid disadvantages.

SUMMARY OF INVENTION

It is an object of the present invention to provide an improved method to effect penis enlargement.

It is a further object of the invention to provide a penis enlargement device of use in the aforesaid method.

Accordingly, in one aspect, the invention provides a penis tensioning device for effecting penis tissue modeling and penis enlargement, said device comprising an elongate tensioning, biasing member having a first portion and a second portion;

first retaining means connected to said first portion and cooperable in tight-fitting engagement with a portion of penis adjacent the glans penis;

second retaining means connected to said second portion and cooperable with a distal member selected from the group consisting of an article of clothing, a body part and an inanimate object.

The glans penis is the medical term for the head of the penis. The term "adjacent the glans penis" includes embodiments wherein the first retaining means is also in engagement with the glans penis.

Accordingly, in one aspect, the invention provides a penis tensioning device for effecting penis tissue remodeling. The tissue remodeling produced by this invention can be directed to free up a portion of the penis attached to the pubic bone to produce an increase penis lengthening when the forces applied have a significant vector component in a downward or backward direction, while all forces generating biologically significant forces within the shaft of the penis will produce the formation of new tissue in the penis and effect a permanent enlargement of the penis.

Preferably, said tensioning biasing member is selected from a coil spring and telescopic biasing means, and more preferably, said tensioning biasing member is formed of an elastics material.

Generally, the device is attached to specific points on clothing that is optionally worn on the chest for creating upward and backward and upward forces. A lower portion that may of an elastics material just fastens above and below the waist. Alternatively, it may be an entirely separate elastic element that is housed in a garment worn on one or both lower extremities to generate forces that are directed in a downward direction that, when engaged, induces a prolonged tensile force being applied to the human penis for use in causing a permanent increase in size of the human penis. As explained in greater detail below, the permanent increase in size is achieved by repeated prolonged application of the device for several hours per day for a few days a week over many weeks, possibly many months.

The tension forces are generally applied daily over a period of 10-12 hours. A minimum of 20-60 minutes per day may be effective for actual growth, but growth overall will be improved with increased duration of daily wear. Preferably, clinically optimal results are achieved with over 6 hours/daily to up to 24 hours/daily).

Preferably, the first retaining means comprises encirclement means for effecting encirclement of said portion of said penis in tight-fitting engagement, Examples of the encirclement means comprises means selected from the group consisting of a ring, cylinder, tube and one or more layers of suitable soft tape material.

Preferably, the second retaining means further comprising third retaining means connectable to a second article of clothing or a second body part wherein said second retaining means comprises an elongate member having a first part, a distal second part and a third part, and wherein said first part is connected to said second portion of said tensioning, biasing member, said distal second part is connectable to said distal member, and said third part connected to said third retaining means.

In alternative embodiments, the device as hereinabove defined further comprising third retaining means connectable to a second article of clothing or a second body part wherein said second retaining means comprises an elongate member having a first part, a distal second part and a third part, and wherein said first part is connected to said second portion of said tensioning, biasing member, said distal second part is connectable to said distal member, and said third part connected to said third retaining means.

Preferably, the device comprising adjusting means wherein said tensioning biasing member is of a length adjustable relative to the length of said second retaining means.

Preferably, the adjusting means comprises adjustable fastening means fastening said tensioning biasing member to said second retaining means at a pre-selected part of said second retaining means.

More preferably, the second retaining means comprises a plurality of said preselected parts, whereby the pre-selection thereof provides said tensioning, biasing member of a pre-selected desired length.

The distal member and the second article are selected from the group consisting of a thigh, leg, foot, waist and shoulder.

The device according to the invention contours to the body and can be worn unobtrusively at all times. This provides convenience, ease of use and dramatically increases the amount of tissue remodeling and, hence, the amount of penile growth induced by this device over other mechanical devices.

The device according to the invention generates forces by attaching itself to parts of the body that are, preferably, relatively long distances away from the penis, and by incorporated a long spring or elastic material, biasing by simply snapping or fixing the elastic device to designated points a wide range of forces can be accurately applied to the penis. In consequence of the relatively long length of these attachments, body movements and changes in body position creates only relatively small dimensional changes in the elastic device result in proportionally small changes.

Suitable selection of the number and locations of the attachment of the second retaining means to the distal member provides for the variation in the direction of the tensile forces created by the tensioning, biasing member to allow of improved direction and localization of tissue remodeling and growth in the penis.

By selection of the location at distal locations, for example, an upper and lower body parts, a longer tensioning member can be used to minimize the variation of length and, hence, minimize the variation in stabilize the magnitude of forces generated. Different angles and force directions can be selected to provide various magnitude of forces, quickly and simply by judicious selection of attachment locations on the distal member(s).

Accordingly, the device may further comprise said second retaining means comprises means connectable to one or more said distal members at one or more selected locations on the same and/or another distal member, simultaneously or otherwise.

Thus, this invention provides the use a biomechanical device that effects a permanent increase in the length and girth of a human penis. As used herein, the term "permanent increase" refers to a long-term increase that lasts for several months or years, or maybe even the life-time of the person.

The term "penis length" refers to the maximum length of the penis, as measured along the dorsal surface of the penis from the symphysis pubis to the tip or end of the glans penis when the glans penis is manually pulled away from the body and put under sufficient tension that the penis is maximally elongated without actually rupturing or tearing the connective tissues. Preferably, the measurement is taken when the penis is flaccid.

The term "penis girth" refers to the largest measured value obtained for circumference of the erect penis, as measured in the thickest region, which is usually the midshaft region, i.e. middle third. Preferably, this measurement is taken when the penis is fully erect.

The device according to the invention comprises biasing means which when operable generates a tensile force. One end of the biasing member is attached to the distal end of the penis, i.e. adjacent the head of the penis formed by the distal portion of the corpus spongiosum. The other end of the biasing means is directly or indirectly attached, most preferably, to a distant part of the body e.g. upper thorax/chest or lower body or ankle/lower leg, such that when the biasing means is operable, a force is generated between the head of the penis and the part of the body which anchors the device.

By varying the location of the body attachment the vector of force acting on the penis can be accurately applied to very specific regions of the penile tissues.

Since the force generated by the biasing means is, in effect, applied to the head of the penis, and the base of the penis is attached to the pubic bone the force will be transmitted from the head of the penis, through the body and midshaft regions of the penis to the fibrous ligaments that anchor the base of the penis to the pubic bone.

The lengthening effects of the forces generated by the device on the penile tissues on the portions of the penis distal to the fibrous ligaments are only mildly altered by changing the direction of the vector of force. In the midshaft and head of the penis, changing the direction of the forces has no effect on the location and distribution of the tensile forces generated within these regions of the penis, and only those proximal areas of the midshaft that are very closely connected and are more directly affected by the fibrous connections to the pubic bone effects are mainly mediated by the changes in the location, distribution and tensile forces generated by the ligaments that attach the penis directly to the pubic bone.

The lengthening and tissue remodeling of the fibrous ligaments that anchor the penis to the pubic bone are highly affected by the direction of the vector of force applied to the penis. Clearly forces in a predominately downward and/or backwards direction have maximal effect in remodeling these fibrous connections to the penis, which effectively frees up a larger portion of the penis.

Forces for which the directional vector of the force being applied that are in an upward and forward direction have a minimal effect when they are applied along the midline axis of the body.

Upward forces that are redirected laterally have an intermediate effect, since the reactive forces generated in these directions cause forces concentrated to loosen and free up the fibres located on the anterior-lateral regions between the penis and the pubic bone. Hence, by alternating these laterally applied upward forces to the right and left side the anterior attachment of the penis can be freed up to effectively lengthen the penis.

Thus, the device according to the invention, by being able to redirect the direction of the applied penile forces to regions entirely different from the fibrous bands of collagen in the penis, is able to stimulate growth in ways and areas of the penis that are unaffected by other devices. The device applies forces to the penis that can dramatically be redirected so that the forces can be able to stimulate growth in regions totally unaffected by unidirectional devices. Hence, the tissue responses, i.e. growth of the penis to these forces can be controlled to specific areas. For example, the device as well as the connective tissue attachments of the penile structures to the body allows the forces to be redirected to different structural components of the penis, including remodeling of the skin to allow the penis to hang much lower in the flaccid state, since the length and size of the flaccid non-erect penis is a major concern and source of embarrassment verbalized by most men wishing to increase the size of their penis.

In summary, the device according to the invention effects penis enlargement through the induction ofussue remodeling and a permanent elongation and growth of the penis by:

1. freeing up some of the important structural connective tissue elements of the anterior portions of the base of the penis which were originally attached to the penis; and 2. elongating and enlarging those parts of body and shaft of the penis that are distal to the fibrous connections between the fibrous ligaments and the base of the penis, and these effects are relatively direction insensitive.

A further advantageous aspect of the invention device is the ability to accurately quantify the magnitude of the forces generated, and allow these forces to be precisely manipulated by changing the activation points, i.e. locations where the elastics are connected to activate the biasing elements, and by locating the anchorage points on the body as far away as possible from the penis, minimizes the percentage change of length any change in body position has on the forces.

I have found that the tension forces created by the device according to the invention which pull the glans penis in a predominately downward and posterior/backwards direction selectively remodels the fibrous connections between the penis and the pubic bone to free up a portion of the penile structures that were originally attached to the pubic bone to produce a permanent increase the length of the penis Importantly, when using prototypes, I have found that with extended wearing, sometimes the forces acting on the penile attachment can induce ischemia, and the patient needs to reduce the tensile forces in order to improve tissue perfusion and prevent ischemic damage to the head and glans penis. Hence, by having multiple attachment points to activate the forces generated by this device, these forces can be readily reduced or completely eliminated during periods of prolonged wearing of this device to reperfuse ischemic tissues. Thus, by periodically reducing pressure on ischemic tissue for brief periods, the magnitude and duration of forces applied to the penis can be dramatically increased and risk to the patient dramatically reduced.

The cellular components of connective tissue and bone are sensitive to mechanical stimuli, possibly through an electrical transduction of the mechanical signal. The tissue cells must then alter their synthesis of the components which constitute the tissue matrix and which determine its mechanical properties. These effects are time dependent.

In all connective tissues, collagen is the principle mechanical component and exists as a fibre reinforcement. Metabolically, collagen is very stable, remodeling very slowly when there is no biological stimulus. Glycosaminoglycans (GAGs) comprise another tissue component which is modified by the cells rapidly. Such modifications are sensitive to applied mechanical loads. These GAGs are also able to modify the mechanical behavior of tissues, which makes them a prime candidate for a biochemical mediator in the biomechanical control loop. It is known that, ultimately, the mechanical forces that induce tissue growth and remodeling act upon the connective tissues to induce cytokine and hormone messages that alter the synthesis of the connective tissue cells causing increased concentrations of proteolytic enzymes, disrupt the collagenous microstructure and activation of the fibroblasts to product new collagen.

In a further aspect, the invention provides a method of effecting penis tissue modeling and penis length and girth enhancement, said method comprising (i) retaining an elongate tensioning biasing member having a first portion and a second portion, at said first portion to the penis adjacent the glans penis in close fitting engagement;

(ii) retaining said second portion to a distal member selected from the group consisting of an article of clothing, a body part or an inanimate object, wherein said length of said biasing member between said first portion and said second portion is such as to operably sufficiently, intermittently provide by exercise as herein defined effective sufficient tension forces to said penis portion as to effect said tissue remodeling.

BRIEF DESCRIPTION OF THE DRAWINGS

In order that the invention may be better understood, preferred embodiments will now be described by way of example only, with reference to the accompanying drawings, wherein

FIGS. 2, 2A and 2B are diagrammatic representations of alternative embodiments of devices according to the invention attached to a wearer;

FIG. 3 is a diagrammatic representation of an adjustable fastening means (in part) of use in a device according to the invention;

FIGS. 4 to 7 are diagrammatic representations of a device according to the invention as fitted to a man at the shoulder, lower leg, chest and back, respectively; and wherein the same numerals denote like parts.

DETAILED DESCRIPTION OF PREFERRED EMBODIMENTS

Figures 1A, 1B:
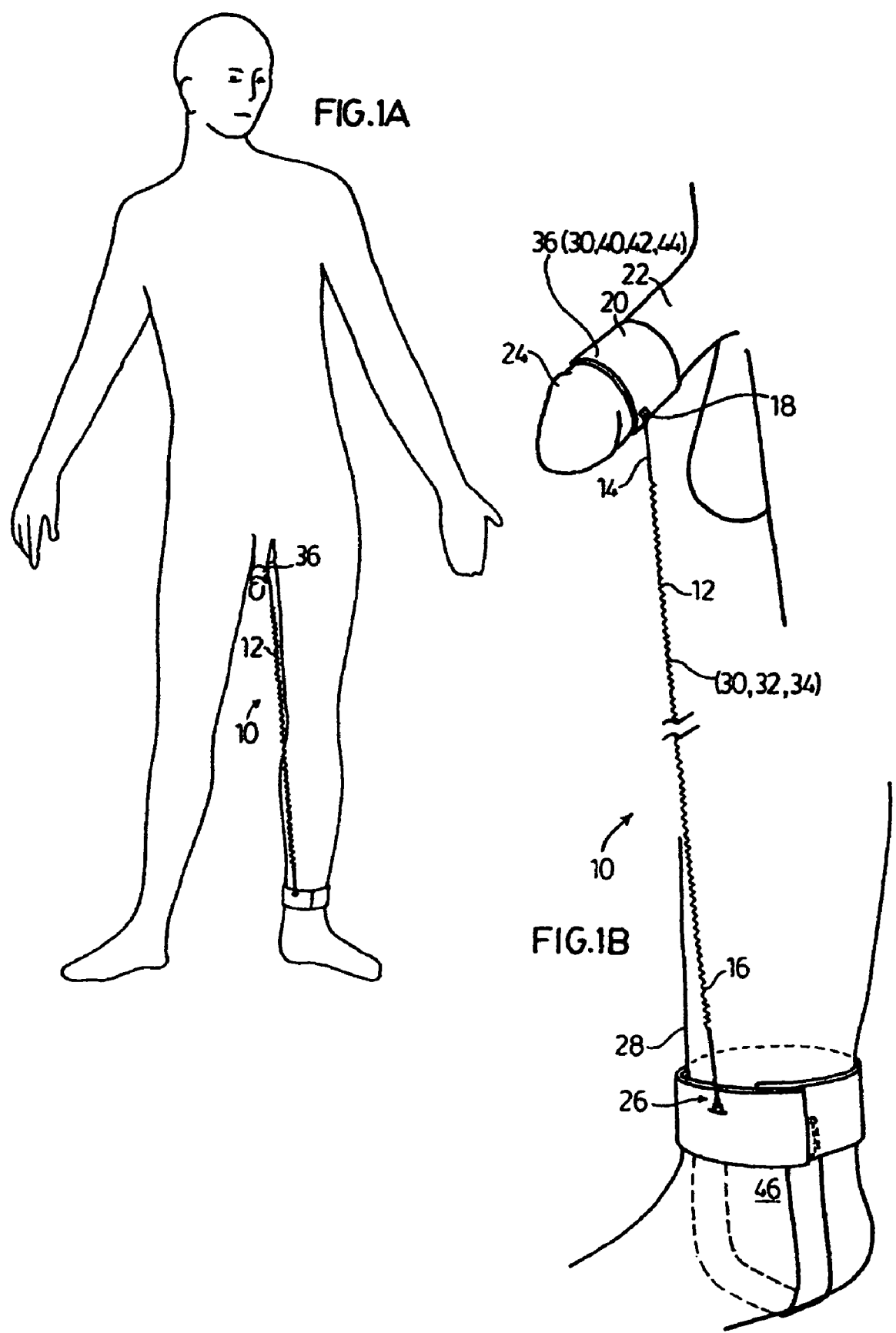
FIGS. 1A and 1B are diagrammatic representations of a penis tensioning device according to the invention affixed to a penis and leg of a wearer.

With reference to FIG. 1, this shows generally as 10 a device having an elongate tensioning member 12 formed of an elastic soft rubber material having a first portion 14 and a second portion 16. First portion 14 is attached to a soft rubber sleeve 18 which embraces portion 22 of penis 22 in tight-fitting engagement adjacent head 24. Second portion 16 is attached by a Velcro™ self-adhering tape 26 to leg 28.

In operation, device 10 is alternatively stretched and retracted under its biasing action to effect stretching and relaxation of penis 22 suitable by movement of leg 28 by the wearer exercising, e.g. walking. This results in penis tissue remodeling and subsequent penis growth.

In an alternative embodiment, FIG. 2 shows generally as 50 a device wherein spring 12 is attached at second portion 16 to elongate member 52, which at part 54 thereof is affixed by a Velcro™ self-adhering tape 58 to upper body 60.

Figure 2B:
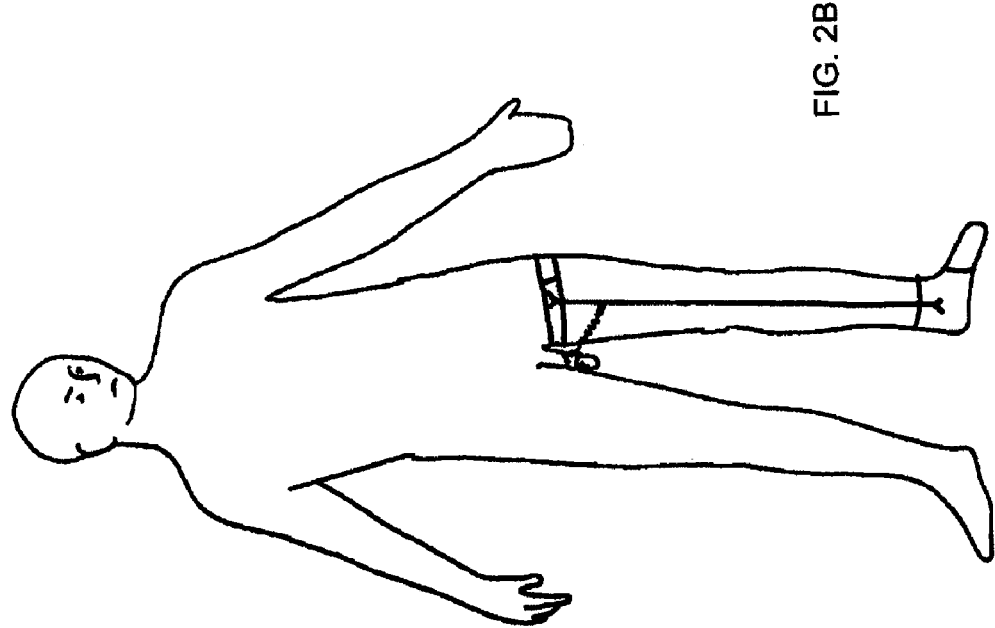
Figure 2A:
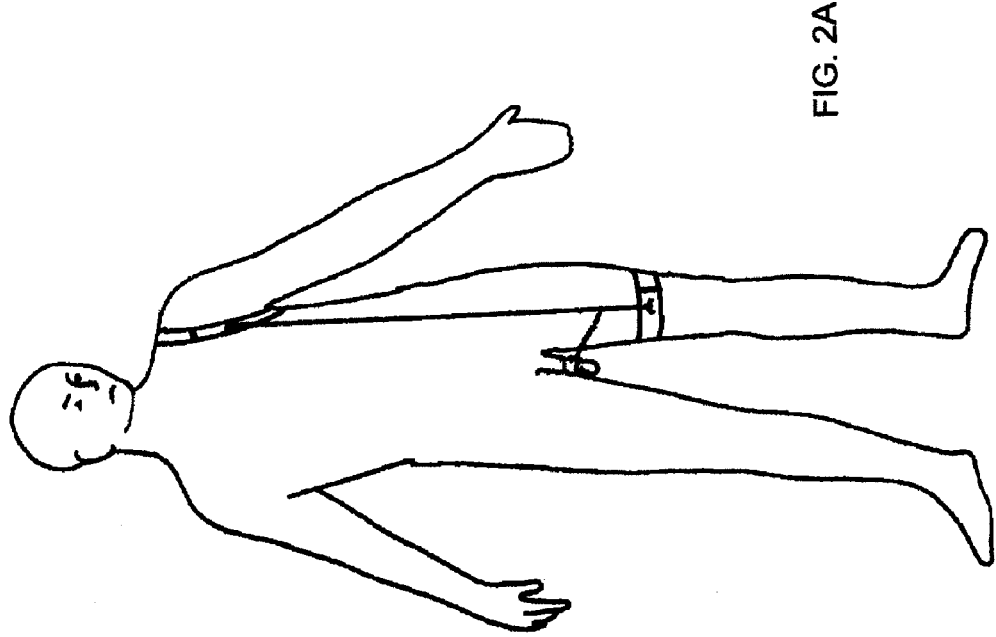

FIGS. 2A and 2B show devices similar to that shown in FIG. 2, but which are attached to different body locations.

FIG. 3 shows generally as 70 an adjustable retaining means consisting of a snap lock assembly of a plurality of longitudinally aligned upstanding studs 74A, 74B, 74C and 74D on retaining means 26 at portion 52 selectively receivable by complementary female cup 76 formed on biasing member 12. Member 12 is suitably retained to penis 22 as hereinabove described.

FIG. 4 shows a loop strap 80 affixed to device 12.

Figure 5:
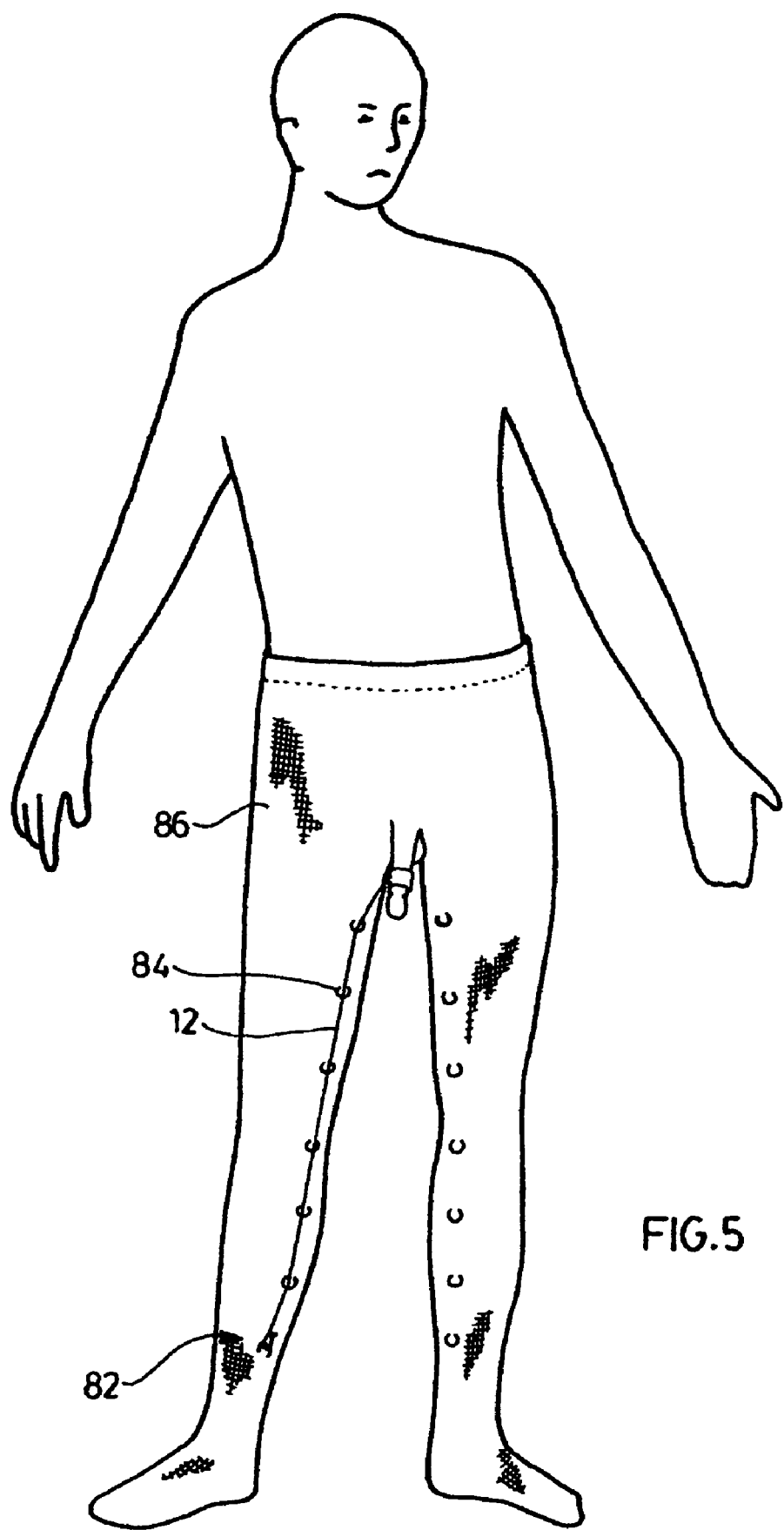

FIG. 5 shows the affixing of device 12 to the lower leg 82 by passage of device 12 through vertically spaced loops 84, attached to undergarment 86.

Figure 6:
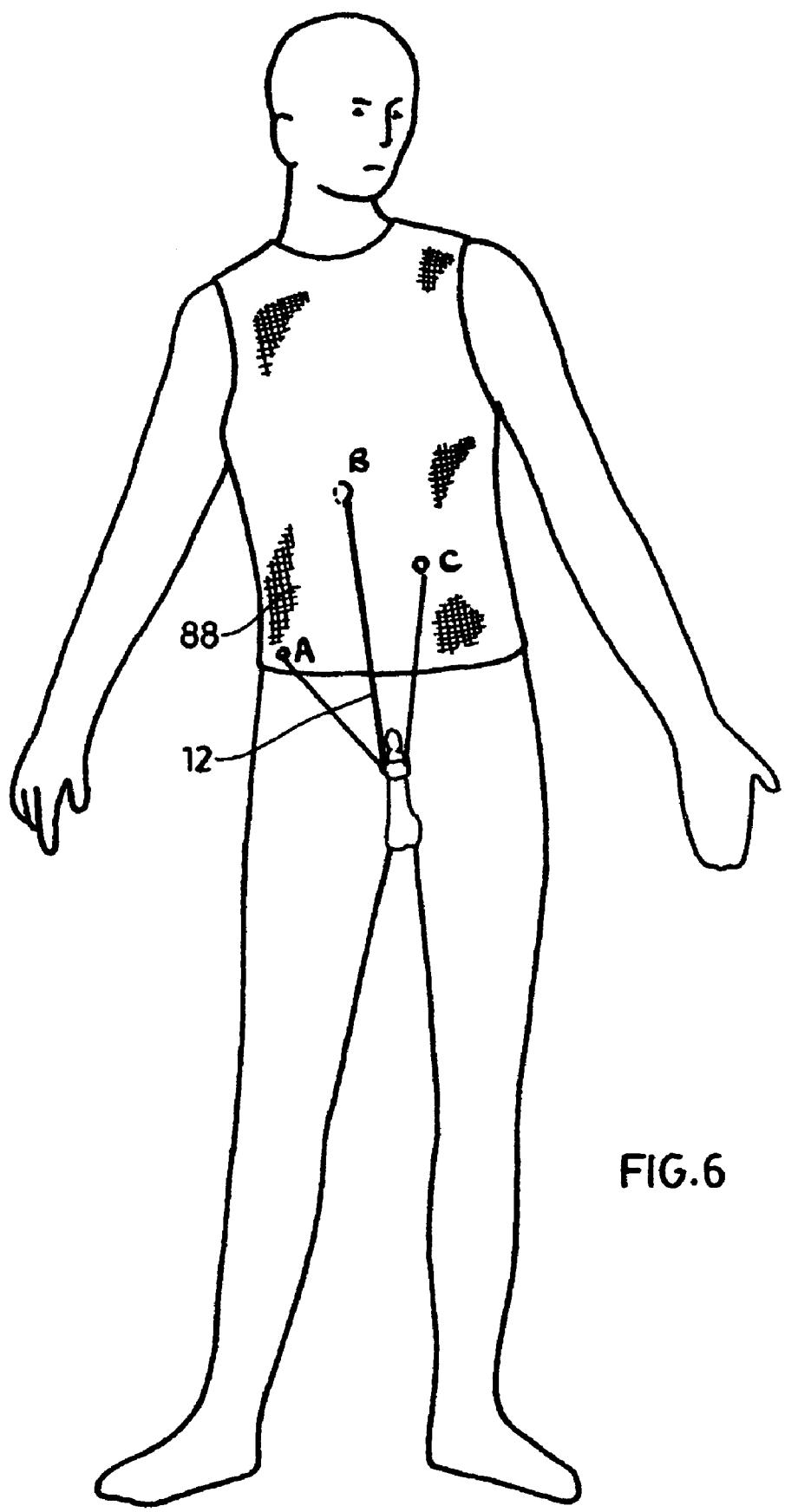

FIG. 6 shows device 12 attached to the front of chest vest 88, at locations A, B and C.

Figure 7:
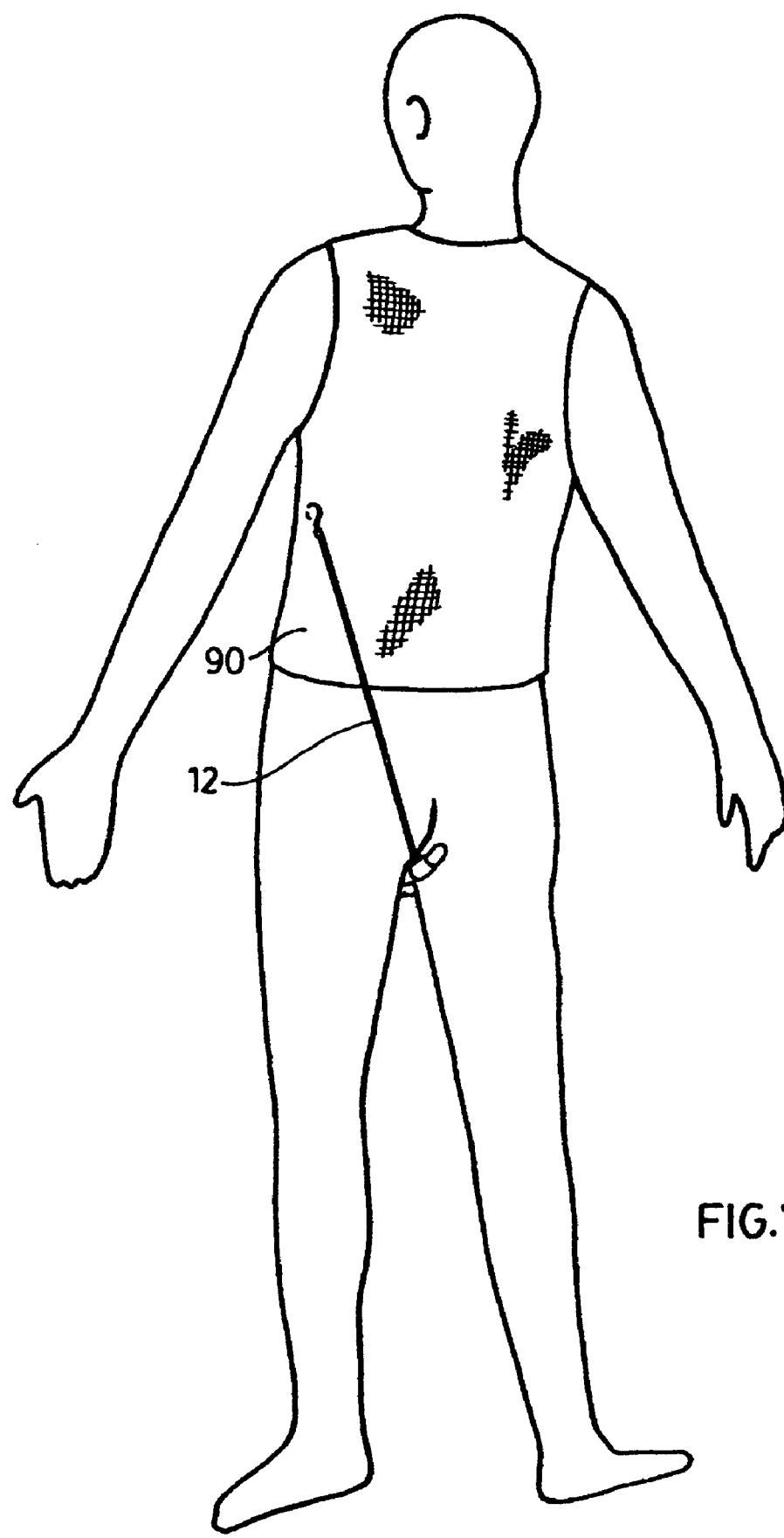

FIG. 7 shows attachment of device 12 to the back 90 of vest 88.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The invention claimed is:

1. A penis tensioning device for effecting penis tissue re-modeling and penis enlargement, said device comprising
    an elongate tensioning, biasing member having a first portion and a second portion;
    first retaining means connected to said first portion and cooperable in tight-fitting engagement with only the portion of the penis adjacent the glans penis;
    second retaining means connected to said second portion and cooperable with a distal member selected from the group consisting of an article of clothing, a body part and an inanimate object; and
    third retaining means connectable to a second article of clothing or a second body part wherein said third retaining means comprises an elongate member having a first part, a distal second part and a third part, and wherein said first part is connected to said second portion of said tensioning, biasing member, said distal second part is connectable to said distal member, and said third part connected to said third retaining means.

2. A device as defined in claim 1 wherein said tensioning biasing member is selected from a coil spring and telescopic biasing means.

3. A device as defined in claim 1 wherein said tensioning biasing member is formed of an elastics material.

4. A device as defined in claim 1 wherein said first retaining means comprises encirclement means for effecting encirclement of said portion of said penis in tight-fitting engagement.

5. A device as defined in claim 1 wherein said encirclement means comprises means selected from the group consisting of a ring, cylinder, tube and one or more layers of suitable soft tape material.

6. A device as defined in claim 1 wherein said second retaining means comprises an encircling member selected from a strap, one or more layers of suitable tape material, and Velcro™ self-adhering material.

7. A device as defined in claim 1 wherein said distal member and said second article is selected from the group consisting of a lower thigh, leg, foot and shoulder.

8. A device as defined in claim 1 wherein said second retaining means comprises means connectable to one or more said distal members at one or more selected locations on the same distal member.

9. A device as defined in claim 1 wherein said second retaining means comprises means connectable to one or more said distal members at one or more selected locations on another distal member.

10. A penis tensioning device for effecting penis tissue re-modeling and penis enlargement, said device comprising
an elongate tensioning, biasing member having a first portion and a second portion;
first retaining means connected to said first portion and cooperable in tight-fitting engagement with only the portion of the penis adjacent the glans penis;
second retaining means connected to said second portion and cooperable with a distal member selected from the group consisting of an article of clothing, a body part and an inanimate object; and
adjusting means wherein said tensioning biasing member is of a length adjustable relative to the length of said second retaining means, wherein said adjusting means comprises adjustable fastening means fastening said tensioning biasing member to said second retaining means at a pre-selected part of said second retaining means, and
wherein said second retaining means comprises a plurality of said pre-selected parts, whereby the pre-selection thereof provides said tensioning, biasing member of a pre-selected desired length.

11. A method of effecting penis tissue modeling and penis length and girth enhancement, said method comprising
(i) retaining an elongate tensioning biasing member having a first portion and a second portion, at said first portion to a penis adjacent the glans penis in close fitting engagement;
(ii) retaining said second portion to an elongate member having a first part, a distal second part and a third part wherein said first part is connected to said second portion of said tensioning, biasing member, said distal second part is connected to a distal member, and said part is connected to a third retaining means, wherein said distal member and said retaining means are selected from the group consisting of an article of clothing, a body part or an inanimate object,
wherein said length of said biasing member between said first portion and said second portion is such as to operably sufficiently, intermittently provide by certain exercise effective sufficient tension forces to said penis portion as to effect said tissue remodeling.

12. A method as defined in claim 11 wherein said tension forces are applied daily over a period of 2-24 hours.

* * * * *